US012042305B2

(12) United States Patent
Chan et al.

(10) Patent No.: US 12,042,305 B2
(45) Date of Patent: Jul. 23, 2024

(54) METHOD FOR ANALYZING ELECTROCARDIOGRAPHY SIGNAL

(71) Applicants: Acer Incorporated, New Taipei (TW); National Yang-Ming University, Taipei (TW)

(72) Inventors: Yun-Hsuan Chan, New Taipei (TW); Ke-Han Pan, New Taipei (TW); Wei-Ju Li, Taipei (TW); Liang-Kung Chen, Taipei (TW); Li-Ning Peng, Taipei (TW)

(73) Assignees: Acer Incorporated, New Taipei (TW); National Yang-Ming University, Taipei (TW)

( * ) Notice: Subject to any disclaimer, the term of this patent is extended or adjusted under 35 U.S.C. 154(b) by 447 days.

(21) Appl. No.: 15/930,453

(22) Filed: May 13, 2020

(65) Prior Publication Data
US 2021/0315473 A1    Oct. 14, 2021

(30) Foreign Application Priority Data

Apr. 10, 2020 (TW) ................. 109112203

(51) Int. Cl.
*A61N 1/00* (2006.01)
*A61B 5/00* (2006.01)
(Continued)

(52) U.S. Cl.
CPC .............. *A61B 5/316* (2021.01); *A61B 5/366* (2021.01); *A61B 5/7257* (2013.01); *A61B 5/726* (2013.01); *A61B 5/7275* (2013.01)

(58) Field of Classification Search
CPC ................. A61B 5/366; A61B 5/368
(Continued)

(56) References Cited

U.S. PATENT DOCUMENTS

| 9,872,652 B2 | 1/2018 | Salehizadeh et al. |
| 2009/0216141 A1* | 8/2009 | Fischell ............... A61B 5/0031 600/509 |

(Continued)

FOREIGN PATENT DOCUMENTS

| TW | I578977 | 4/2017 |
| TW | I663958 | 7/2019 |
| WO | 2019046854 | 3/2019 |

OTHER PUBLICATIONS

Divya Shanmugam et al., "Multiple Instance Learning for ECG Risk Stratification", Machine Learning for Health (ML4H) Workshop at NeurIPS 2018, Mar. 24, 2020, pp. 1-5.
(Continued)

*Primary Examiner* — Nicole F Lavert
(74) *Attorney, Agent, or Firm* — Edell, Shapiro & Finnan, LLC

(57) ABSTRACT

A method for analyzing an electrocardiography (ECG) signal is provided. The ECG signal is measured through a sensor. One or more specified waveforms in the ECG signal are detected. Multiple ECG features from each specified waveform are captured. The ECG features are input into multiple candidate models to obtain multiple candidate scores. Each candidate score is compared with a standard value to obtain an ideal score among the candidate scores. One of the candidate models corresponding to the ideal score is selected as a risk prediction model to predict disease risk through the risk prediction model.

9 Claims, 5 Drawing Sheets

(51) Int. Cl.
*A61B 5/316* (2021.01)
*A61B 5/366* (2021.01)

(58) Field of Classification Search
USPC .......................................... 600/508
See application file for complete search history.

(56) References Cited

U.S. PATENT DOCUMENTS

| | | | | |
|---|---|---|---|---|
| 2012/0123232 | A1* | 5/2012 | Najarian | G16Z 99/00 600/407 |
| 2014/0371610 | A1 | 12/2014 | Liu et al. | |
| 2016/0135706 | A1* | 5/2016 | Sullivan | A61B 5/316 600/509 |
| 2017/0238847 | A1* | 8/2017 | Inan | A61B 5/02125 |

OTHER PUBLICATIONS

Sushravya Raghunath et al., "Deep neural networks can predict mortality from 12-lead electrocardiogram voltage data", arxiv.org, Apr. 15, 2019, pp. 1-11.

Omid Rajabi Shishvan et al., "Machine Intelligence in Healthcare and Medical Cyber Physical Systems: A Survey", IEEE Access, Sep. 7, 2018, pp. 46419-46494.

Aditya Khosla et al., "An integrated machine learning approach to stroke prediction", Proceedings of the 16th ACM SIGKDD International Conference on Knowledge Discovery and Data Mining, Jul. 25, 2010, pp. 1-9.

"Search Report of Europe Counterpart Application", dated Oct. 26, 2020, pp. 1-11.

\* cited by examiner

METHOD FOR ANALYZING ELECTROCARDIOGRAPHY SIGNAL

CROSS-REFERENCE TO RELATED APPLICATION

This application claims the priority benefit of Taiwan application serial no. 109112203, filed on Apr. 10, 2020. The entirety of the above-mentioned patent application is hereby incorporated by reference herein and made a part of this specification.

BACKGROUND

Technical Field

The disclosure relates to a disease prediction method, and in particular to a method for analyzing an electrocardiography (ECG) signal.

Description of Related Art

In modern life, the prevention of heart disease is becoming more and more important. If the heart disease can be detected and treated early, there will be better effects. Therefore, predicting the risk of heart disease has become an important issue. In the prior art, most predictions of heart disease risk use risk factors to establish models, such as using age, total cholesterol, high-density cholesterol, blood pressure, smoking or non-smoking, diabetes, etc. to establish the Cox proportional hazards model to predict the risk of heart disease. However, obtaining the risk factors of the condition inside the body using certain invasive methods is resisted by some people, thereby rejecting going to the hospital for examination.

In the past, doctors usually use changes in the ECG to help identify the type of heart disease from different waveform features. The sources for collecting ECG data are all from equipment in the hospital, but the ECG examined in the hospital can only determine the condition at that moment and cannot be instantly measured when people are feeling unwell.

SUMMARY

The disclosure provides a method for analyzing an electrocardiography (ECG) signal, which can replace the use of risk factors to establish a model for prediction.

The method for analyzing the ECG signal of the disclosure includes the following steps. The ECG signal is measured through a sensor. One or more specified waveforms in the ECG signal are detected. Multiple ECG features from each specified waveform are captured. The ECG features are input into multiple candidate models to obtain multiple candidate scores. Each candidate score is compared with a standard value to obtain an ideal score among the candidate scores. One of the candidate models corresponding to the ideal score is selected as a risk prediction model to predict disease risk through the risk prediction model.

In an embodiment of the disclosure, the step of comparing each candidate score with the standard value includes the following steps. A mean absolute percentage error between each candidate score and the standard value is calculated. The candidate score corresponding to a smallest among the mean absolute percentage error is used as the ideal score.

In an embodiment of the disclosure, the method for analyzing the ECG signal further includes the following step. The standard value is obtained through a proportional risk model.

In an embodiment of the disclosure, the specified waveform includes a first wave, a second wave, and a third wave, wherein an amplitude of the third wave is greater than amplitudes of the first wave and the second wave. After the specified waveform in the ECG signal is detected, whether a relative positional relationship between the first wave and the second wave of each specified waveform is the same as the relative positional relationship between the first wave and the second wave of other specified waveforms is determined to judge the ECG signal as abnormal when relative positions of the first wave and the second wave of one of the specified waveforms are different from the relative positions of the first wave and the second wave of other specified waveforms.

In an embodiment of the disclosure, the step of detecting the specified waveform in the ECG signal includes the following steps. A first spacing mean, a first spacing standard deviation, and a root mean square of first spacing sum of squares between the third waves of two adjacent specified waveforms are calculated. A second spacing mean, a second spacing standard deviation, and a root mean square of second spacing sum of squares between the first wave and the second wave of each specified waveform are calculated. The first spacing mean, the first spacing standard deviation, the root mean square of first spacing sum of squares, the second spacing mean, the second spacing standard deviation, and the root mean square of second spacing sum of squares are used as ECG features.

In an embodiment of the disclosure, the step of inputting the ECG features into the candidate models to obtain the candidate scores includes the following step. Multiple basic feature and ECG features are input into the candidate models, wherein the basic feature includes basic features such as gender, age, body mass index, blood pressure value, smoking index, etc.

In an embodiment of the disclosure, the method for analyzing the ECG signal further includes the following step. Whether the ECG signal is saturated is determined; and the ECG signal is abandoned if the ECG signal is saturated.

In an embodiment of the disclosure, the step of determining whether the ECG signal is saturated includes the following step. Whether a signal value in the ECG signal exceeds a preset value is determined; and the ECG signal is judged as saturated if the signal value exceeds the preset value.

In an embodiment of the disclosure, the method for analyzing the ECG signal further includes the following step. The ECG signal is cut into multiple signal segments to detect the specified waveform in each signal segment.

In an embodiment of the disclosure, after the ECG signal is measured through the sensor, a pre-processing is performed on an original ECG signal. The pre-processing includes the following steps. An interpolation is used to add one or more missing values, when the original ECG signal is judged as having a missing signal, to obtain a first pre-processing signal. The first pre-processing signal is adjusted to a fixed length to obtain a second pre-processing signal. A smoothing process is performed, after removing displacement of the second pre-processing signal, to obtain an ECG signal after pre-processing.

Based on the above, the disclosure is combined with the ECG signal to capture features from the ECG signal to predict the risk of heart disease, so as to replace the use of risk factors to establish a model for prediction as in the past. As such, the time taken for people to go to the hospital for examination can be saved without limitation to live while taking care of health.

To make the aforementioned and other features of the disclosure more comprehensible, several embodiments accompanied with drawings are described in detail as follows.

DETAILED DESCRIPTION OF DISCLOSED EMBODIMENTS

Figure 1:
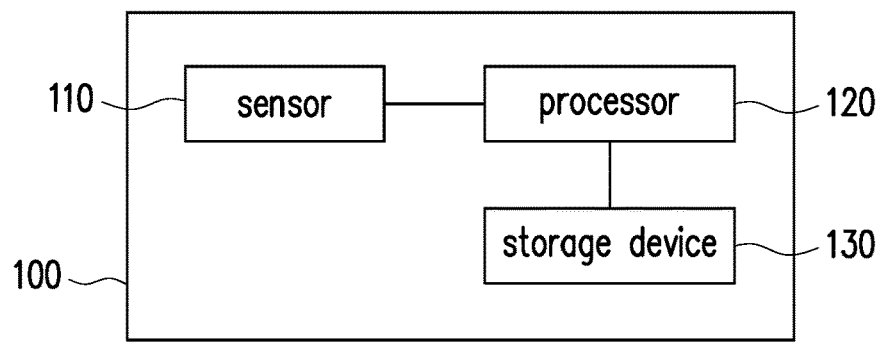
FIG. 1 is a block diagram of an electronic device according to an embodiment of the disclosure.

FIG. 1 is a block diagram of an electronic device according to an embodiment of the disclosure. Referring to FIG. 1, an electronic device 100 includes a sensor 110, a processor 120, and a storage device 130. The processor 120 is coupled to the sensor 110 and the storage device 130. Here, the electronic device 100 may be a wearable device and the sensor 110 is, for example, an electrocardiography (ECG) instrument. The user wears the electronic device 100 on the body for the sensor 110 to measure the position of an ECG signal.

The processor 120 is, for example, a central processing unit (CPU), a physics processing unit (PPU), a programmable microprocessor, an embedded control chip, a digital signal processor (DSP), an application specific integrated circuits (ASIC), or other similar devices.

The storage device 130 is, for example, any type of fixed or removable random access memory (RAM), read-only memory (ROM), flash memory, hard disk, other similar devices, or a combination of the aforementioned devices. Multiple code snippets are stored in the storage device 130. The code snippets are performed by the processor 120 after being installed to implement the following method for analyzing the ECG signal.

Figure 2:
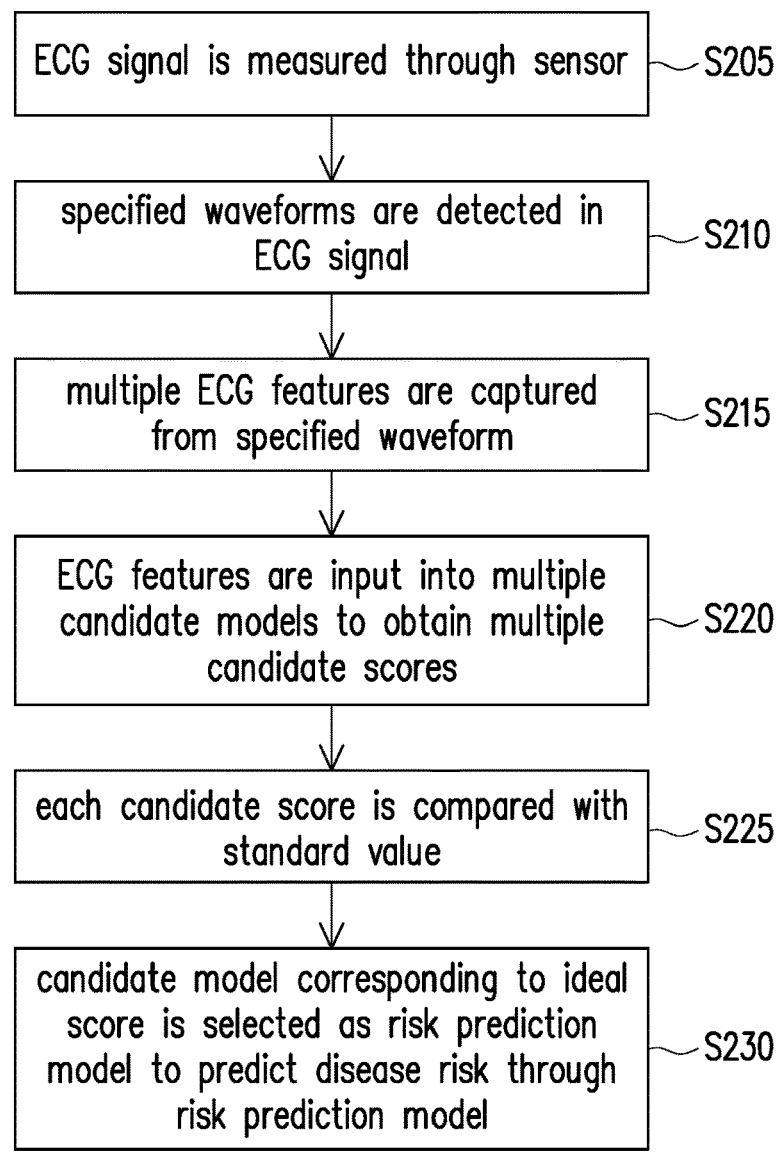
FIG. 2 is a flowchart of a method for analyzing an electrocardiography (ECG) signal according to an embodiment of the disclosure.

FIG. 2 is a flowchart of a method for analyzing an ECG signal according to an embodiment of the disclosure. Referring to FIG. 2, in Step S205, the ECG signal is measured through the sensor 110. The processor 120 may first determine whether the ECG signal is saturated. If the ECG signal is saturated, the ECG signal is abandoned. For example, whether a signal value in the ECG signal exceeds a preset value and remains constant is determined. If the signal value exceeds the preset value and remains constant, the ECG signal is judged as saturated.

Next, in Step S210, the processor 120 detects a specified waveform in the ECG signal. The specified waveform includes a first wave, a second wave, and a third wave, wherein an amplitude of the third wave is greater than amplitudes of the first wave and the second wave. Here, the specified waveform is a QRS wave, the third wave is an R wave, and the first wave and the second wave are respectively a Q wave and an S wave.

Generally speaking, in a normal cardiac cycle, the ECG signal has three types of more significant waveforms, that is, a P wave, the QRS wave, and a T wave. The ECG signal is formed from the three types of waves continuously appearing. The P wave represents the depolarization of the atrium, the QRS wave represents the depolarization of the ventricle, and the T wave represents the repolarization of the ventricle. The QRS wave is a waveform formed from the Q wave, the R wave, and the S wave.

Here, after the processor 120 receives the ECG signal from the sensor 110, in order to facilitate processing, the ECG signal may be first cut into multiple signal segments to respectively detect the specified waveforms in the signal segments. For example, a signal region is cut every 6 seconds.

In the embodiment, the ECG signal obtained will have more noise. Therefore, the processor 120 may first reduce the interference of capturing waveform features through the algorithm of signal time-frequency conversion. In addition, the processor 120 will further perform a pre-processing on an original ECG signal. The pre-processing includes: determining whether there is a missing signal in the original ECG signal. If there is a missing signal, one or more missing values are first added by an interpolation to obtain a first pre-processing signal. After that, the first pre-processing signal is adjusted to a fixed length to obtain a second pre-processing signal. Next, the smoothing cubic spline is used on the second pre-processing signal to remove displacement of the second pre-processing signal and a smoothing process is performed to obtain an ECG signal after pre-processing. The smoothing process eliminates signal noise so that the signal is smooth by using, for example, the fast Fourier transform and the Butterworth filter. Then, the wavelet transform may be used on the ECG signal after the pre-processing to analyze the waveform of the normal cardiac cycle and capture the position of the specified waveform in the ECG signal. That is, the processor 120 performs the wavelet transform on the ECG signal, thereby increasing the intensity of the QRS wave to be detected. Then, a threshold value is defined, signals below the threshold value are eliminated, and a highest point in the unelimated signals is found as the position of the R wave. The Q wave and the S wave are medically defined as lowest points respectively found within a range of 0.01×sampling rate on the left and right sides of the R wave position (that is, the respective widths of the Q wave and the S wave with the R wave is within 0.01 s).

Figure 3:
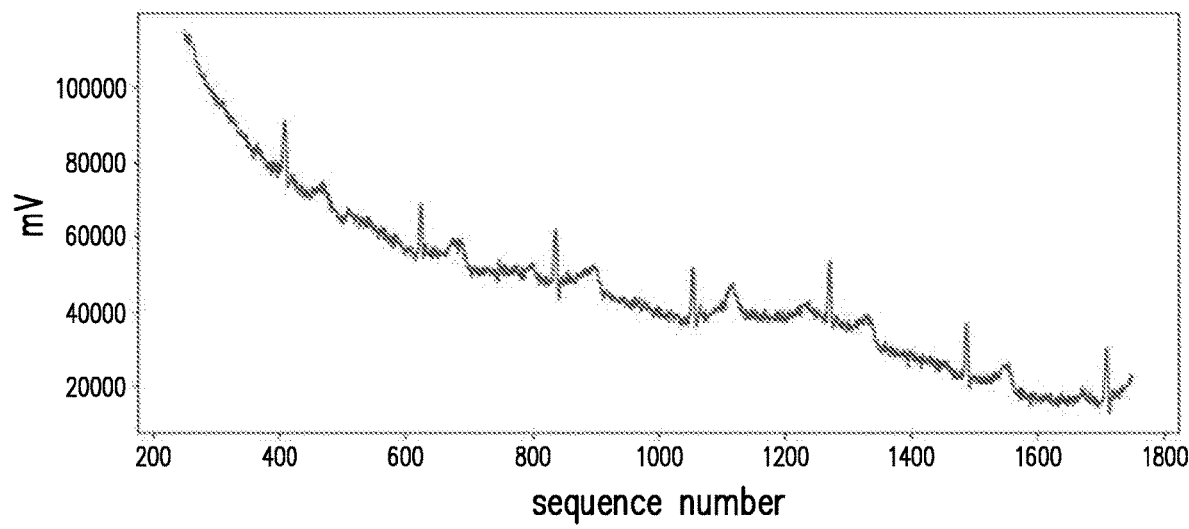
FIG. 3 is a schematic diagram of an original ECG signal according to an embodiment of the disclosure.
Figure 4:
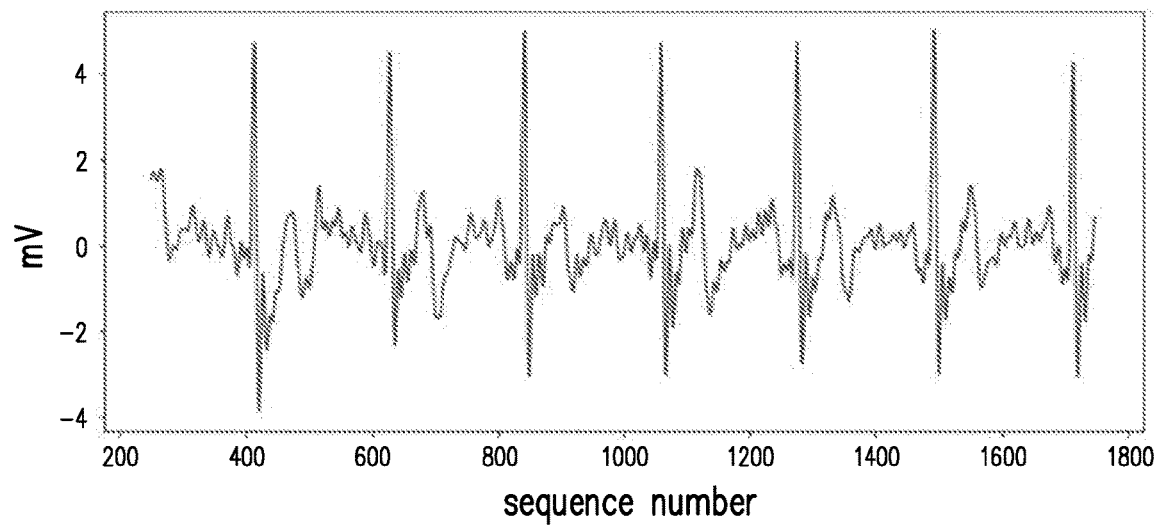
FIG. 4 is a schematic diagram of an ECG signal after pre-processing according to an embodiment of the disclosure.

FIG. 3 is a schematic diagram of an original ECG signal according to an embodiment of the disclosure. FIG. 4 is a schematic diagram of an ECG signal after pre-processing according to an embodiment of the disclosure. It can be clearly seen from FIG. 3 and FIG. 4 that the position of the specified waveform in the ECG signal after pre-processing (as shown in FIG. 4) may more easily detected.

In addition, since it is impossible to ensure whether the operating or recording environment of the electronic device 100 will affect the quality of signal measurement, causing the signal to be an abnormal ECG signal, thereby affecting the subsequent analysis results, the QRS wave detected may be further used to determine whether the ECG signal is abnormal. That is, after the specified waveform is detected, the specified waveform is analyzed to determine whether the ECG signal is abnormal. Here, the processor 120 determines whether a relative positional relationship between the first wave and the second wave of each specified waveform is the same as the relative positional relationship between the first wave and the second wave of other specified waveforms, so that the ECG signal is judged as abnormal when relative positions of the first wave and the second wave of one of the specified waveforms are different from the relative positions of the first wave and the second wave of other specified waveforms.

Specifically, under normal circumstances, if the Q wave of one set of the QRS wave is higher than the S wave, the Q waves of other sets of QRS waves will also be higher than the S waves; conversely, if the Q wave of one set of the QRS wave is lower than the S wave, the Q waves of other sets of QRS waves will also be lower than the S waves.

In addition, the R wave may be further used to convert the heart rate to determine whether the heart rate is within a preset range (for example, 40 to 180 bpm). If the heart rate falls within the preset range, the ECG signal is judged as normal. If the heart rate does not fall within the preset range, the ECG signal is judged as abnormal.

Returning to FIG. 2, after the specified waveform is found, in Step S215, the processor 120 captures multiple ECG features from each specified waveform. In the embodiment, the processor 120 calculates a first spacing mean, a first spacing standard deviation, and a root mean square of first spacing sum of squares between the third waves of two adjacent specified waveforms. Also, the processor 120 calculates a second spacing mean, a second spacing standard deviation, and a root mean square of second spacing sum of squares between the first wave and the second wave of each specified waveform. The processor 120 uses the first spacing mean, the first spacing standard deviation, the root mean square of first spacing sum of squares, the second spacing mean, the second spacing standard deviation, and the root mean square of second spacing sum of squares as the ECG features.

Figure 5:
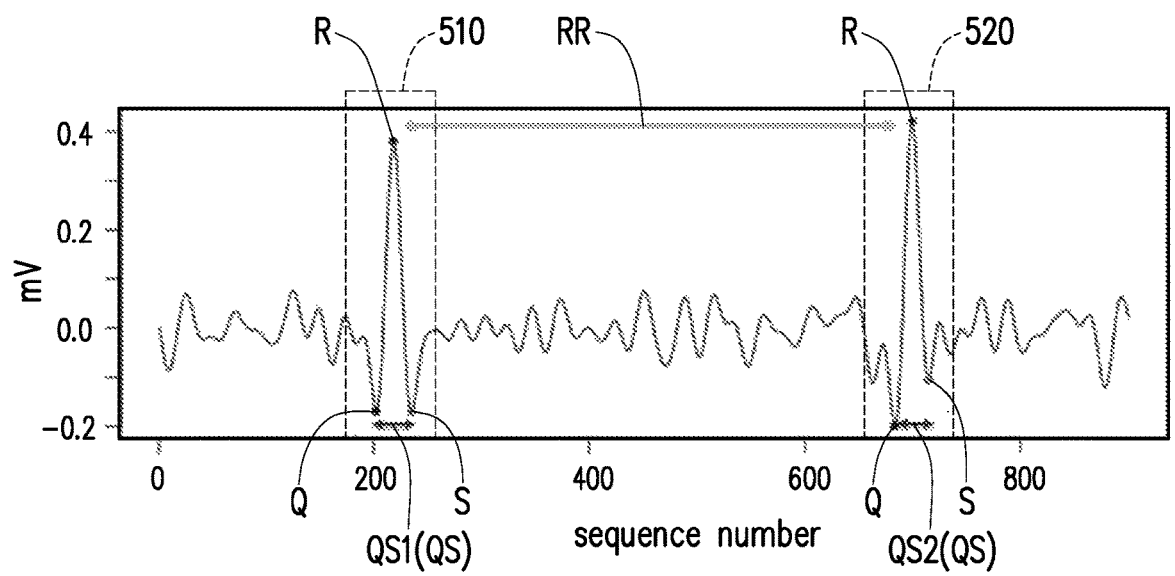
FIG. 5 is a schematic diagram of QRS waves according to an embodiment of the disclosure.

FIG. 5 is a schematic diagram of QRS waves according to an embodiment of the disclosure. FIG. 5 shows a QRS wave 510 and a QRS wave 520 as examples for illustration. The QRS wave 510 and the QRS wave 520 respectively have three points, Q, R, and S (hereinafter referred to as Q wave, R wave, and S wave).

After detecting the positions of the QRS wave 510 and the QRS wave 520, the processor 120 further calculates a first spacing RR between the R waves of the two adjacent QRS wave 510 and QRS wave 520, a second spacing QS1 between the Q wave and the S wave of the QRS wave 510, and a second spacing QS2 (second spacings are collectively referred to as QS hereinafter) between the Q wave and the S wave of the QRS wave 520 The first spacing mean, the first spacing standard deviation, and the root mean square of first spacing sum of squares respectively are, for example, the mean, standard deviation, and root mean square of sum of squares between the first spacings RR of multiple QRS waves. The second spacing mean, the second spacing standard deviation, and the root mean square of second spacing sum of squares respectively are, for example, the mean, standard deviation, and root mean square of sum of squares between the Q wave and the S wave of each of the multiple QRS waves. Here, the normal time limit of the first spacing RR is about 0.6 to 1.0 seconds to see whether the mean heart rate is within a reasonable range. The normal time limit of the second spacing QS is about 0.08 to 0.10 seconds to see whether the Q wave and the S wave are within a reasonable range. The remaining standard deviation, root mean square, etc. are all indicators to determine whether the ECG signal is stable.

After that, in Step S220, the processor 120 inputs the ECG features into multiple candidate models to obtain multiple candidate scores. In the process of establishing a risk prediction model, two types of methods, a machine learning model and a deep learning model, are adopted. In addition to the ECG features captured from the ECG signal after pre-processing, a basic feature is also adopted. The basic feature includes at least one of gender, age, body mass index (BMI), blood pressure value, and smoking index. The smoking index represents whether the patient has a habit of smoking. In establishing the future risk prediction model, there are two ways, that is, the machine learning model and the deep learning model, which will be exemplified in the following.

Figure 6:
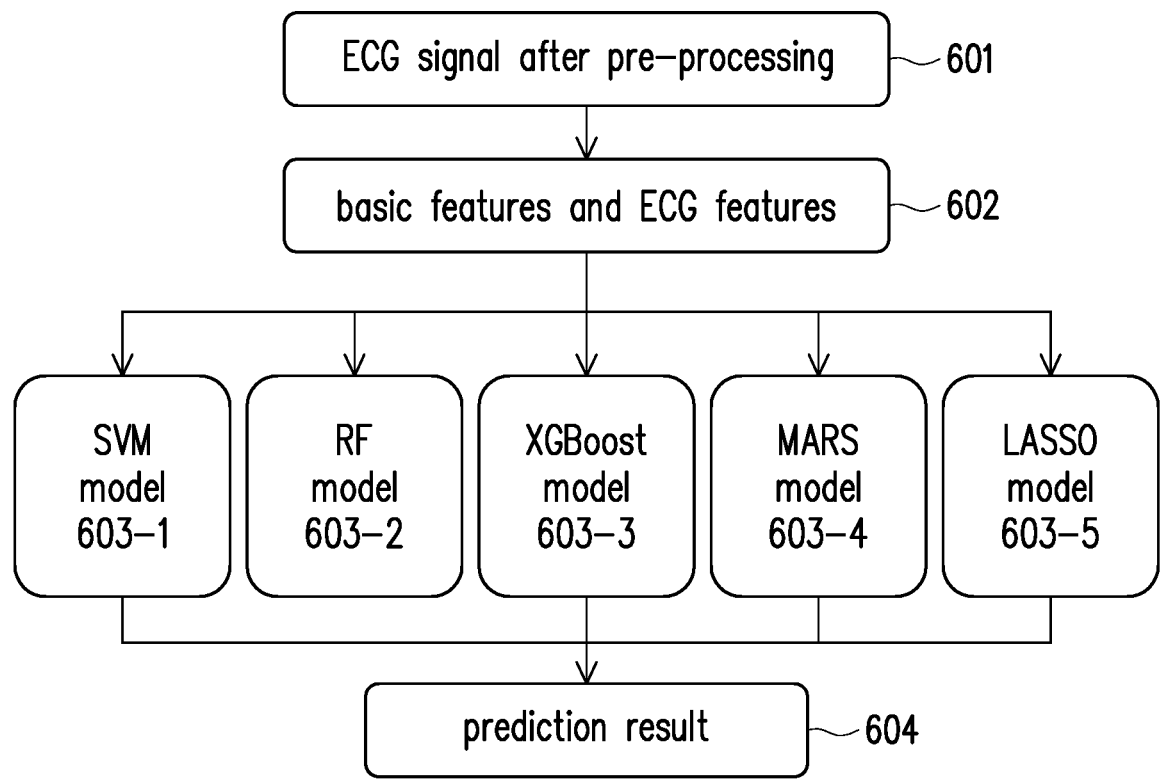
FIG. 6 is a flowchart of a machine learning model according to an embodiment of the disclosure.

FIG. 6 is a flowchart of a machine learning model according to an embodiment of the disclosure. In FIG. 6, machine learning models such as a support vector machine (SVM) model 603-1, a random forest (RF) model 603-2, an eXtreme gradient boosting (XGBoost) model 603-3, a multivariate adaptive regression splines (MARS) model 603-4, a least absolute shrinkage and selection operator (LASSO) model 603-5, etc. are adopted. The ECG features are captured from an ECG signal after pre-processing 601. After that, a basic feature and ECG features 602 are input into the respective machine learning models (603-1 to 603-5), thereby obtaining multiple prediction results (candidate scores) 604.

Figure 7:
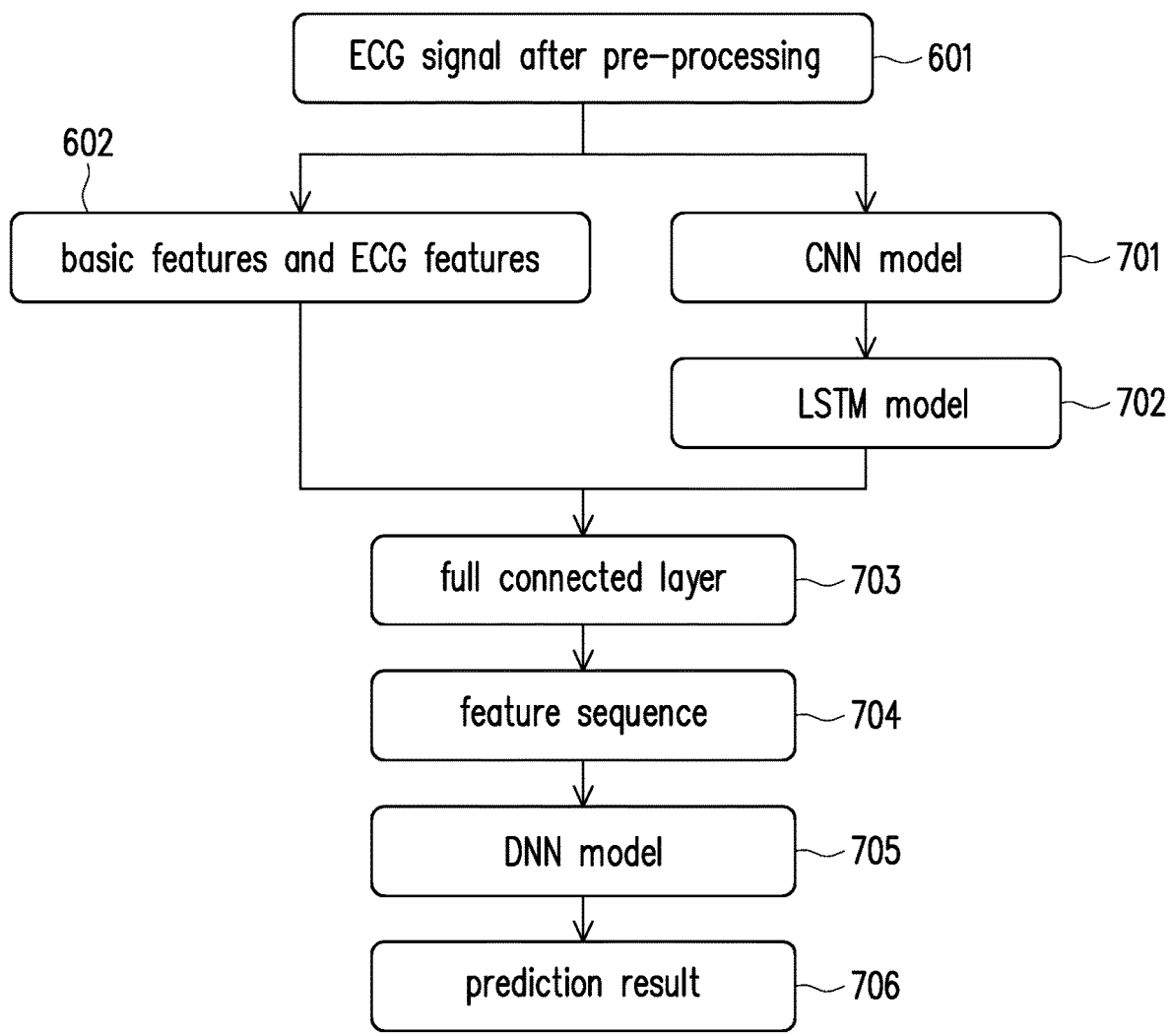
FIG. 7 is a flowchart of a deep learning model according to an embodiment of the disclosure.

In the deep learning method, the differences from the machine learning model method are that in addition to putting the basic feature and ECG features 602, the sequence of the ECG signal may also be directly put in the deep learning model, so that in addition to learning the ECG features captured, the deep learning model may also automatically capture important signal features from the ECG signal. Referring to FIG. 7, the ECG signal after pre-processing 601 is put in a one-dimensional convolutional neural network (CNN) model 701 before putting in a long-short term memory (LSTM) model 702 to establish features relevant to sequence order. Next, the features relevant to the sequence are connected with the basic feature and ECG features 602 through a full connected layer 703 to obtain a feature sequence 704. After that, the feature sequence 704 is input into a deep neural networks (DNN) model 705, thereby obtaining a prediction result (candidate score) 706.

Returning to FIG. 2, in Step S225, the processor 120 compares each candidate score with a standard value to obtain an ideal score from the candidate scores. For example, the mean absolute percentage error (MAPE) between each candidate score and the standard value is calculated and the candidate score corresponding to a smallest among the MAPE is used as the ideal score. The standard value is obtained through a conventional model, such as a proportional risk model. Then, a cross-validation is performed multiple times (for example, 10 times) to validate the stability of the model before selecting the candidate model with a smaller MAPE. In addition, the ideal score may also be determined by calculating the candidate scores multiple times.

After that, in Step S230, the processor 120 selects the candidate model corresponding to the ideal score as the risk prediction model to predict disease risk through the risk prediction model.

In summary, the disclosure is combined with the ECG signal to capture features from the ECG signal to predict the risk of heart disease, so as to replace the use of risk factors to establish a model for prediction as in the past. As such, the time taken for people to go to the hospital for examination can be saved without limitation to live while taking care of health. Moreover, a wearable device may be used to measure the ECG, instantly monitor the health condition of the heart, and predict the future risk of heart disease using the method, so as to warn the user of early treatment in the case where a high risk is predicted.

Although the disclosure has been disclosed in the above embodiments, the embodiments are not intended to limit the disclosure. It will be apparent to persons skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A method for analyzing an electrocardiography (ECG) signal, comprising:
   measuring an ECG signal through an electrocardiography instrument set in a wearable electronic device, and transmitting the ECG signal to a processor included in the wearable electronic device, and using the processor to perform following steps:
   detecting a plurality of QRS waves in the ECG signal, wherein each of the QRS waves includes a Q wave, an R wave and an S wave, an amplitude of the R wave is greater than amplitudes of the Q wave and the S wave;
   in response to a relative positional relationship between the Q wave and the S wave of each of the QRS waves is the same as the relative positional relationship between the Q wave and the S wave of other QRS waves, judging the ECG signal as a normal signal, wherein an amplitude of the Q wave is higher than an amplitude of the S wave in each of the QRS waves with the same relative positional relationship, or the amplitude of the Q wave is lower than the amplitude of the S wave in each of the QRS waves with the same relative positional relationship;
   calculating a spacing between every two adjacent R waves in a plurality of R waves included in the QRS waves to obtain a plurality of first spacings;
   calculating a first spacing mean, a first spacing standard deviation, and a root mean square of first spacing sum of squares for the plurality of first spacings;
   calculating a spacing between the Q wave and the S wave included in each of the QRS waves to obtain a plurality of second spacings corresponding to the QRS waves respectively;
   calculating a second spacing mean, a second spacing standard deviation, and a root mean square of second spacing sum of squares for the plurality of second spacings;
   using the first spacing mean, the first spacing standard deviation, the root mean square of first spacing sum of squares, the second spacing mean, the second spacing standard deviation, and the root mean square of second spacing sum of squares as a plurality of ECG features;
   inputting the plurality of ECG features into a plurality of trained candidate models to obtain a plurality of candidate scores, wherein the trained candidate models are trained by at least one of a machine learning model and a deep learning model;
   comparing each of the candidate scores with a standard value to obtain an ideal score among the plurality of candidate scores;
   selecting one of the trained candidate models corresponding to the ideal score as a risk prediction model to predict disease risk through the risk prediction model; and
   automatically warn, by the wearable electronic device and based on an output of the risk prediction model. a user of the wearable electronic device to seek treatment for a heart condition.

2. The method for analyzing an ECG signal according to claim 1, wherein the step of comparing each of the candidate scores with the standard value comprises:
   calculating a mean absolute percentage error between each of the candidate scores and the standard value; and
   using a candidate score corresponding to a smallest among the mean absolute percentage error as the ideal score.

3. The method for analyzing an ECG signal according to claim 2, further comprising:
   obtaining the standard value through a proportional risk model.

4. A method for analyzing an ECG signal, comprising:
   measuring an ECG signal through an electrocardiogramstrument set in a wearable electronic device, and transmitting the ECG signal to a processor included in the wearable electronic device, and using the processor to perform following steps:
   detecting a plurality of QRS waves in the ECG signal, wherein each of the ORS waves includes a Q wave, an R wave and an S wave, an amplitude of the R wave is greater than amplitudes of the Q wave and the S wave;
   in response to a relative positional relationship between the Q wave and the S wave of each of the ORS waves is the same as the relative positional relationship between the Q wave and the S wave of other ORS waves, judging the ECG signal as a normal signal, wherein an amplitude of the Q wave is higher than an amplitude of the S wave in each of the ORS waves with the same relative positional relationship, or the amplitude of the Q wave is lower than the amplitude of the S wave in each of the QRS waves with the same relative positional relationship;
   calculating a spacing between every two adjacent R waves in a plurality of R waves included in the QRS waves to obtain a plurality of first spacings;
   calculating a first spacing mean, a first spacing standard deviation, and a root mean square of first spacing sum of squares for the plurality of first spacings;
   calculating a spacing between the Q wave and the S wave included in each of the QRS waves to obtain a plurality of second spacings corresponding to the QRS waves respectively;
   calculating a second spacing mean, a second spacing standard deviation, and a root mean square of second spacing sum of squares for the plurality of second spacings;
   using the first spacing mean, the first spacing standard deviation, the root mean square of first spacing sum of squares, the second spacing mean, the second spacing standard deviation, and the root mean square of second spacing sum of squares as a plurality of ECG features:
   inputting the plurality of ECG features into a plurality of trained candidate models to obtain a plurality of candidate scores, wherein the trained candidate models are trained by at least one of a machine learning model and a deep learning model;

comparing each of the candidate scores with a standard value to obtain an ideal score among the plurality of candidate scores;

selecting one of the trained candidate models corresponding to the ideal score as a risk prediction model to predict disease risk through the risk prediction model; and automatically warn, by the wearable electronic device and based on an output of the risk prediction model, a user of wearable electronic device to seek treatment for a heart condition, wherein after detecting the QRS waves in the ECG signal, using the processor to perform following steps:

determining whether the relative positional relationship between the Q wave and the S wave of each of the QRS waves is the same as the relative positional relationship between the Q wave and the S wave of other QRS waves, so that the ECG signal is judged as abnormal when relative positions of the Q wave and the S wave of one of the QRS waves are different from the relative positions of the Q wave and the S wave of other QRS waves.

5. The method for analyzing an ECG signal according to claim 1, wherein the step of inputting the plurality of ECG features into the plurality of candidate models to obtain the plurality of candidate scores comprises:

inputting a basic feature and the plurality of ECG features into the plurality of candidate models, wherein the basic feature comprises at least one of a gender, an age, a body mass index, a blood pressure value, and a smoking index.

6. The method for analyzing an ECG signal according to claim 1, further comprising:

determining whether the ECG signal is saturated; and
abandoning the ECG signal if the ECG signal is saturated.

7. The method for analyzing an ECG signal according to claim 1, wherein the step of determining whether the ECG signal is saturated comprises:

determine whether a signal value in the ECG signal exceeds a preset value; and
judging the ECG signal as saturated if the signal value exceeds the preset value.

8. A method for analyzing an ECG signal comprising:

measuring an ECG signal through an electrocardiogramstrument set in a wearable electronic device, and transmitting the ECG signal to a processor included in the wearable electronic device, and using the processor to perform following steps:

cutting the ECG signal into a plurality of signal segments to detect a plurality of QRS waves in each of the signal segments, wherein each of the QRS waves includes a Q wave, an R wave and an S wave, an amplitude of the R wave is greater than amplitudes of the Q wave and the S wave;

in response to a relative positional relationship between the Q wave and the S wave of each of the QRS waves is the same as the relative positional relationship between the Q wave and the S wave of other QRS waves, judging the ECG signal as a normal signal, wherein an amplitude of the Q wave is higher than an amplitude of the S wave in each of the QRS waves with the same relative positional relationship, or the amplitude of the Q wave is lower than the amplitude of the S wave in each of the QRS waves with the same relative positional relationship;

calculating a spacing between every two adjacent R waves in a plurality of R waves included in the QRS waves to obtain a plurality of first spacings;

calculating a first spacing mean, a first spacing standard deviation, and a root mean square of first spacing sum of squares for the plurality of first spacings;

calculating a spacing between the Q wave and the S wave included in each of the ORS waves to obtain a plurality of second spacings corresponding to the ORS waves respectively:

calculating a second spacing mean, a second spacing standard deviation, and a root mean square of second spacing sum of squares for the plurality of second spacings;

using the first spacing mean, the first spacing standard deviation, the root mean square of first spacing sum of squares, the second spacing mean, the second spacing standard deviation, and the root mean square of second spacing sum of squares as a plurality of ECG features;

inputting the plurality of ECG features into a plurality of trained candidate models to obtain a plurality of candidate scores, wherein the trained candidate models are trained by at least one of a machine learning model and a deep learning model;

comparing each of the candidate scores with a standard value to obtain an ideal score among the plurality of candidate scores;

selecting one of the trained candidate models corresponding to the ideal score as a risk prediction model to predict disease risk through the risk prediction model; and automatically warning, by the wearable electronic device and based on an output of the risk prediction model, a user of wearable electronic device to seek treatment for a heart condition.

9. The method for analyzing an ECG signal according to claim 1, wherein the step of measuring the ECG signal through the electrocardiography instrument comprises:

performing a pre-processing on an original ECG signal, the pre-processing comprising:

using an interpolation to add one or more missing values, when the original ECG signal is judged to have a missing signal, to obtain a first pre-processing signal;

adjusting the first pre-processing signal to a fixed length to obtain a second pre-processing signal; and performing a smoothing process, after removing displacement of the second pre-processing signal, to obtain the ECG signal after pre-processing.

* * * * *